United States Patent [19]
Hoffmann

[11] Patent Number: 5,534,488
[45] Date of Patent: Jul. 9, 1996

[54] INSULIN FORMULATION

[75] Inventor: James A. Hoffmann, Greenwood, Ind.

[73] Assignee: Eli Lilly and Company, Indianapolis, Ind.

[21] Appl. No.: 106,106

[22] Filed: Aug. 13, 1993

[51] Int. Cl.$^6$ .................................................. A61K 38/28
[52] U.S. Cl. ........................ 514/3; 514/4; 530/303; 530/304
[58] Field of Search ............................ 514/3, 4; 530/304

[56] References Cited

U.S. PATENT DOCUMENTS

| | | |
|---|---|---|
| 2,626,228 | 5/1948 | Petersen . |
| 2,799,622 | 7/1957 | Schlichtkrull et al. . |
| 2,819,999 | 1/1958 | Schlichtkrull et al. . |
| 2,849,370 | 8/1958 | Petersen et al. . |
| 2,882,202 | 4/1959 | Petersen et al. . |
| 2,882,203 | 4/1959 | Petersen et al. . |
| 3,060,093 | 10/1962 | Poulsen et al. . |
| 3,102,077 | 8/1963 | Christensen et al. . |
| 4,476,118 | 10/1984 | Brange et al. ............................ 424/178 |
| 5,070,186 | 12/1993 | Joergensen .............................. 530/304 |
| 5,177,058 | 1/1993 | Dorschug ..................................... 514/4 |

FOREIGN PATENT DOCUMENTS 539091  9/1984  Australia .

OTHER PUBLICATIONS

Kirk–Othmer, Encyclopedia of Chemical Technology, 3rd Ed., vol. 13, John Wiley and Sons, NY 1981, pp. 607–614.
Diamant et al., Subcutaneous absorption of insulin in insulin dependent diabetic patients, Dan. Med. Bull., 38:4, 337–346 (1991).
Skyler, Insulin Treatment, Therapy for Diabetes Mellitus and Related Disorders, American Diabetes Assoc., Alexandria, VA, 127–137 (1991).
Tattersall, Bovine Insulin, BMJ, 305, 831 (1992).
Seigler et al., Pharmacokinetics of long–acting (ultralente) insulin preparations, Diabetes Nutrition & Metabolism, 4, 267–273.
Graham et al., An in–vitro test for the duration of action in insulin suspensions, J. Pharm. Pharmacol. 36, 427–430 (1984).
Francis et al., Human Ultralete Insulin, Diabetes Research, 3, 263–268 (1986).
Freeman et al., Use of human ultralente as the basal insulin component in treatment of patients with IDDM, Diabetes. Res. and Clin. Practice, 12, 187–192 (1991).
Fontbonne, Insulin–A Sex Hormone for Cardiolvascular Risk, Circulation, 84, 1442–1444 (1991).
Owens et al., Human, Procine and Bovine Ultralente Insulin:Subcutaneous Administration in Normal Man, Diabetic Medicine, 3, 326–329 (1986).
Holman et al., Human Ultralente Insulin, British Med. J., 288, 665–668 (1984).
Atkinson et al., Genetic Control of the Immune Response to Insulin, Insulin Action, 2, 183–192 (1989).

Hirsch et al., Intensive Insulin Therapy:Part I. Basic Principles, Amer. Family Physician, 45:5, 2141–2147 (1992).
Keen et al., Human Insulin Produced by Recombinant DNA Technology:Safety and Hypoglycaemic Potency in Healthy Men, The Lancet, 398–401 (1980).
Makita et al., Advanced Glycosylation End Products in Patents with Diabetic Nephropathy, The New England J. of Med., 836–842 (1991).
Arslanian et al., Etiology of the Dawn Phenomenon, Diab. Care, 15:7, 928–929 (1992).
Jorgensen et al., NovoSol Basal:Pharmacokinetics of a Novel Soluble Long Acting Insulin Analogue, BMJ, 299, 415–419 (1989).
Hansen, The self–association of zinc–free human insulin and insulin analogue B13–glutamine, Biophysical Chemistry, 39, 107–110 (1991).
Brange et al., Monomeric Insulins and Their Experimental and Clinical Implicaitons, Diab. Care, 13:9, 923–954 (1990).
Home et al., Bioavailability of Highly Purified Bovine Ultralente Insulin, Diab. Care, 6:2, 210 (1983).
Owens, Long–acting Insulin Preparations, Human Insulin Clinical Pharmacological Studies in Normal Man, 170–177 (1986).
Reeves et al., Insulin Antibodies Induced by Bovine Insulin Therapy, Clin. Exp. Immunol., 50, 163–170 (1982).
Walford et al., The Effect of Insulin Antibodies on Insulin Dose and Diabetic Control, Diabetologia, 22, 106–110 (1982).
Schlichtkrull, Chemical and Biological Studies on Insulin Crystals and Insulin Zinc Suspensions, Insulin Crystals (1958).
Hallas–Møller et al., Cystalline and Amorphous Insulin-–Zinc Compounds with Prolonged Action, Science, 116, 394–398 (1952).
Brange et al., Galenics of Insulin; The Physico–chemical and Pharmaceutical Aspects of Insulin and Insulin Preparations (1987).
Brange et al., Chemical Stability of Insulin. 1. Hydrolytic Degradation During Storage of Pharmaceutical Preparations, Pharma. Res. 9:6, 715–726 (1992).

Primary Examiner—Jill Warden
Assistant Examiner—David Lukton
Attorney, Agent, or Firm—Steven P. Caltrider; Douglas K. Norman; Gerald V. Dahling

[57] ABSTRACT

The present invention is directed to an insulin formulation comprising a suspension of Ultralente crystals and a total formulation zinc concentration of between about 0.5 milligrams to about 20 milligrams per 100 units of insulin. Greater than fifty percent of the total zinc in the formulation resides in the soluble fraction, rather than in complex with the insulin. This insulin formulation generally has a pH from between about 6.0 to about 7.4. In addition, the insulin formulation of the present invention does not contain other proteins like protamine. This zinc-modified formulation displays characteristics of a very long lasting human insulin product.

19 Claims, No Drawings

INSULIN FORMULATION

FIELD OF THE INVENTION

The present invention is in the field of human medicine, particularly in the treatment of diabetes. Most specifically, the invention relates to formulations comprising the human insulin molecule which when administered, more closely mimic the basal levels of insulin found in the normal human body.

BACKGROUND OF THE INVENTION

A major therapeutic goal in the treatment of diabetes is the physiological control of blood glucose levels. Many different commercial products and formulations are available for this purpose. For the rapid rise in glucose challenge that occurs at mealtimes, the fast-acting insulin products, such as Humulin Regular or the so-called monomeric insulin analogs are most appropriate.

Another important source of glucose load in patients is the low-level, basal glucose output from the liver. This output results primarily from postprandial metabolic processes such as gluconeogenesis and glycogenolysis. In diabetic subjects, this basal glucose output can increase substantially at night and result in extended periods of hyperglycemia, especially during the early morning hours in an incident referred to as the dawn phenomenon. These periods of hyperglycemia have been shown to be an important contributor to high levels of glycated proteins, often measured clinically as glycosylated hemoglobin. Buildup of these derivatized protein products is implicated in the long-term complications associated with diabetes such as neuropathy, nephropathy and retinopathy.

The ideal insulin formulation to deal with this basal glucose output would be one that resulted in a slow, steady infusion of insulin into the bloodstream that matched the low level of glucose output from the liver. In terms of this ideal basal time action, the best parenteral product that fits this description is commercially available beef Ultralente insulin. Injected just once per day, it gives a low, steady release of insulin into the bloodstream without any noticeable insulin peak.

A major problem with beef Ultralente, however, stems from the fact that beef insulin is different in amino acid sequence from human insulin. The human body can recognize bovine insulin as a foreign protein. Chronic injection of this immunogenic substance in diabetic patients can result in the formation of antibodies to the insulin. This can lead to alterations in insulin time action and potency and other problems arising from the patient's activated immune system. For these reasons beef Ultralente remains a non-ideal parenteral insulin formulation.

Species Differences in Ultralente Insulins

The advent of recombinant DNA technology and novel enzymatic techniques for converting pork insulin into human insulin both resulted in abundant supplies of human insulin becoming available beginning in 1980. To overcome the problems associated with beef Ultralente noted above, a logical step was the preparation of human Ultralente crystals and their formulation into a commercially available, parenteral formulation. The crystal forms, crystal shapes, crystal sizes, method of preparation and formulation compositions of human and beef Ultralente products are essentially identical.

However, several years of clinical experience led to definite indications that these products were not identical. In fact, clinical reports indicated that human Ultralente was faster acting than the beef Ultralente formulation while pork Ultralente was shown to be intermediate in time action between the other two species. In clinical practice this has led many physicians and diabetologists to recommend a twice a day injection protocol for human Ultralente. In addition, a significant peak of insulin absorption into the blood stream is observed about 12 hours after subcutaneous administration. This phenomena not only diminishes the ability of this product to counteract the steady basal glucose output of the liver, it also results in hyperinsulinemia which itself may lead to macrovascular complications.

The reasons for the differences in time action between human and beef Ultralente products are not completely understood. The presence of antibodies to the beef insulin is not the primary cause for this difference in time action. Some research has shown that the insulin from human Ultralente was more quickly absorbed from the injection site than beef Ultralente. Further insight into this question has come from dissolution assays described further in this patent specification. Based on modifications of previously described assays, these dissolution tests have shown that the beef Ultralente crystal, upon dilution, simply takes much longer to dissolve than the comparable human Ultralente crystal. Differences in the amino acid sequences between beef and human insulin likely generate slight differences in the insulin hexamer packing in the crystals that result in differences in their subsequent solvation rates. After injection into the subcutaneous tissue, this delay in dissolution of the beef crystals likely leads to its more prolonged absorption and biological time action.

The synthesis of human insulin analogs is one way in which prolongation of time action has been explored. In particular, modifications such as Gly$^{(A21)}$Arg$^{(B27)}$Thr-NH$_2^{(B30)}$ human insulin (Jorgensen et.al., *British Medical Journal* 299, 415–419 (1989)) and modifications at the Glu$^{(B13)}$ position (Hansen, *Biophysical Chemistry* 39, 107–110 (1991)) have been made. However, in each of these cases the introduction of a new amino acid sequence renders the molecule foreign to the human body and therefore potentially just as immunogenic or even more immunogenic than beef insulin. Clearly, using the natural human insulin molecule would be better than introduction of a new insulin molecule. In any case, no highly zinc-enriched human Ultralente formulations nor means of preparing such formulations for the purpose of prolonging the time action of the immunologically preferred human Ultralente formulation to equal or better the biological time action of the pharmacokinetically preferred beef Ultralente formulation have been reported.

Zinc and Insulin

It has been known for many years that insulin can be successfully co-crystallized with zinc atoms to obtain numerous types of stable crystals with longer time actions than soluble or amorphous, uncrystallized insulin. The fish protein protamine has also been used as an insulin complexation agent to prolong the time action of insulin, but its heterogeneity and potential for immunogenicity make it less attractive for a medicine chronically administered subcutaneously.

In the early 1950s a new formulation of beef insulin crystals was developed which contained only insulin and zinc in an acetate buffer at neutral pH (Hallas-Moller, et.al.,

*Science* 116, 394–398 (1952)). This Lente insulin avoided phosphate ions, which interact strongly with zinc ions to form insoluble zinc phosphate derivatives. Formulations containing only the crystalline insulin in acetate buffer are called Ultralente. Crystals prepared in this manner will be referred to here as Ultralente insulin crystals.

Although only 2 zinc atoms are required to be complexed within each insulin hexamer to form the proper Ultralente crystals, a defined molar excess of zinc is in each Ultralente formulation and was found to be appropriate in giving beef Ultralente a one injection per day time action (Schlichtkrull, in Insulin Crystals, Ejnar Munksgaard Publishers, Copenhagen (1958)). This same work (p. 92) reported, "It appears that the duration of action is somewhat shortened when pig insulin is substituted for beef insulin in the Ultralente. Hence, in order to secure a constant timing of the therapeutic suspensions, it is necessary to adhere strictly to one and the same species or to find a fixed proportion between insulin from different species." Similarly, it was reported that pork Ultralente insulin was more quickly absorbed in diabetics than beef Ultralente insulin (Brange, in *Galenics of Insulin*, p. 28, Springer-Verlag, Berlin (1987)). However, even though these species differences were noted, and pig insulin is closer to the structure of human insulin and therefore less immunogenic then beef insulin, possible formulation changes to prolong the time action of pig Ultralente to make it equivalent to or longer than beef Ultralente have been neither demonstrated nor proposed. In fact, an earlier report (Hallas-Moller, *Diabetes* 5, 7–12 (1956)) suggested that zinc levels above 0.2 mg per 100 insulin units would not aid in further prolonging the time action of Lente (or Ultralente) insulin formulations of any species.

Approximately 0.09 mg of zinc per 100 units of insulin is reported to be bound up with the insoluble beef Ultralente crystals (14 zinc atoms per insulin hexamer) while a relatively low free zinc concentration of about 0.05 mg per ml remains unbound in the supernatant. Both of these levels are designed to remain constant even as the insulin formulation strength is increased from 40 U/ml to 100 U/ml (Brange, in *Galenics of Insulin*, p. 37, Springer-Verlag, Berlin (1987)).

In a recent US patent specification (U.S. Pat. No. 5,070,186) it was reported that insulin formulations containing a high concentration (0.02–0.5M) of another divalent metal cation, magnesium, resulted in quicker-acting insulin products. However, it has now been surprisingly discovered that adding solid or concentrated aqueous solutions of zinc chloride or acetate directly to the human Ultralente formulation to a final total zinc concentration of about 0.5 to 20 mg per 100 units of insulin delays the dissolution of the crystals and can prolong its biological time action to be as slow or even slower than that of beef Ultralente. It was also discovered that this modification resulted in a concomitant drop in pH from about pH 7.4 to as low as pH 6.2. It was further discovered that this modification resulted in most of the added zinc residing in the supernatant and unbound to the insoluble insulin crystal. It also did not significantly alter the apparent shape or size of the crystals or the chemical stability of the insulin in the formulations after certain periods of storage.

SUMMARY OF THE INVENTION

The present invention is directed to an insulin formulation comprising a suspension of Ultralente insulin crystals in a total formulation zinc concentration of between about 0.5 milligrams to about 20 milligrams per 100 units of insulin. Greater than fifty percent of the total zinc in the formulation resides in the soluble fraction, rather than in complex with the insulin. This insulin formulation generally has a pH from between about 6.0 to about 7.4. This zinc-modified formulation displays characteristics of a very long lasting human insulin product.

For purposes of the present invention, as disclosed and claimed herein, the following terms and abbreviations are as defined below.

Total formulation zinc concentration—the entire concentration of zinc within the formulation, whether said zinc is complexed with the insulin or is in the soluble form.

Ultralente insulin—formulations containing insulin crystals prepared in acetate buffer in substantial accordance with the teaching of Hallas-Moller, et al., *Science* 116, 394–398 (1952). Crystals prepared in this manner will be referred to here as Ultralente insulin crystals.

U—the standard international unit of insulin activity.

Zn—zinc.

All amino acid abbreviations used in this disclosure are those accepted by the United States Patent and Trademark Office as set forth in 37 C.F.R. §1,822(b) (2) (1990).

DETAILED DESCRIPTION OF THE INVENTION

The present invention is directed to an insulin formulation comprising a suspension of Ultralente crystals in a total formulation zinc concentration of between about 0.5 milligrams to about 20 milligrams per 100 units of insulin. Greater than fifty percent of the total zinc in the formulation resides in the soluble fraction, rather than in complex with the insulin. This insulin formulation generally has a pH from between about 6.0 to about 7.4. In addition, the insulin formulation of the present invention does not contain other proteins like protamine. The formulation may contain preservatives or isotonicity agents and it also may contain a buffer which does not strongly interact with zinc. This zinc-modified formulation displays characteristics of a very long lasting human insulin product.

The formulations of the present invention can be made by adding zinc to previously prepared suspensions of Ultralente insulin crystals or by adding extra zinc after the crystallization step of the actual Ultralente manufacturing process. The zinc may be added in solid form or it may be added as a solution. Alternatively, a suspension of Ultralente crystals can be added to the solid zinc or to the zinc solution. Several different zinc salts can be used in the present invention. Representative examples of zinc salts include zinc acetate, zinc bromide, zinc chloride, zinc fluoride, zinc iodide and zinc sulfate. The skilled artisan will recognize that there are many other zinc salts which also might be used in the production of the zinc-modified Ultralente insulin formulations of the present invention. Preferably, zinc acetate or zinc chloride is used to create the zinc-modified Ultralente insulin formulations of the present invention as these salts do not add new chemical ions to commercially available Ultralente formulations.

The invention described herein, therefore, is directed at substantially increasing the concentration of zinc in the supernatant of human Ultralente formulations without significantly modifying the Ultralente crystals themselves. It was surprisingly found that this zinc-enriched Ultralente formulation can delay the dissolution rate of the insoluble insulin crystals and prolong the biological time action compared to unmodified human Ultralente formulations.

Avoiding a dramatic modification of the Ultralente crystal may be important for several reasons. First, Ultralente formulations have been used in chronic administration to diabetics for 40 years now and human Ultralente itself for nearly 10 years. Hence, a record of safety can be drawn upon with these new zinc-modified formulations. Second, substantially increasing the zinc level in complexation with insulin crystals could lead to aggregation of the crystals. Over periods of time, this could form clumps in the formulation that render it unusable. Examinations of the zinc-modified human Ultralente insulin formulations described in this invention revealed no significantly modified or clumped insulin crystals. Finally, modification of the zinc-insulin crystal could lead to alteration of the insulin structure itself that could alter its biological properties or even its immunogenicity.

The concomitant drop in pH that occurs in the preparation of these modified Ultralente formulations may also be important. Increasing the level of soluble zinc ions is known to increase the chemical cleavage of insulin between the A8 {threonine) and A9 (serine) residues, even when the insulin is present as insoluble crystals, (Brange, et.al., *Pharmaceutical Research* 9, 715–726 (1992)). Slightly lowering the pH of insulin formulations below pH 7 minimizes this cleavage reaction and hence long-term stability is improved. It is also possible that this pH drop may be partly responsible for the minimal interaction of the excess zinc with the insulin crystal, as protein interactions with zinc are known to be reduced at more acidic pHs, (Schlichtkrull, in *Insulin Crystals*, Ejnar Munksgaard Publishers, Copenhagen (1958)).

The new zinc-modified human Ultralente formulations described in this invention have several additional attributes. The method of formulation can take place long after the original human Ultralente formulation was prepared. Various levels of zinc could even be added in this manner at a pharmacy or clinic and be tailored, depending on the desired time action, to the needs of individual patients. Also, no new excipients, complexing agents, chemicals or organic solvents are needed for these formulations, so concerns regarding unknown toxicity of chronic administration of new chemical entities for many years are avoided. Finally, the pH range of the final solution, pH 6.0 to 7.4, is close enough to the pH of the subcutaneous tissue (pH 7.4) that no irritation should result.

The present invention provides formulations of human Ultralente crystals suitable for treating diabetes by subcutaneous injection, such injections giving a slow absorption of insulin such that, if desired, no more than one injection per day needs to be administered. The formulations may also contain a preserving agent, such as methyl paraben, an isotonicity agent such as sodium chloride and a total zinc content of about 0.5 to 20 mg per 100 insulin units and the pH is from about 6.0 to 7.4. The skilled artisan will recognize that many other preservatives and isotonicity agents are available for use in the present invention. In a preferred embodiment, the total zinc concentration is about 0.5 to 7 mg per 100 insulin units and the pH is from about 6.2 to 7.2. Another preferred embodiment is a pH for all zinc levels that results when the appropriate quantity of solid zinc chloride, solid zinc acetate or a concentrated aqueous solution of these reagents is added to a pre-formulated human Ultralente solution, i.e., no further pH adjustments are made.

For comparison of zinc and insulin concentrations noted in other literature and patent documents, Table I sets forth the equivalency of zinc and insulin in combination while Table II sets forth the equivalency of zinc in solution.

TABLE I

Zinc/Insulin Combination

| mEq Zn/g of insulin | % Zn in anhydrous insulin crystal | µM Zn/ µM insulin | µM Zn/µM insulin hexamer | mg Zn/100 insulin units | µg (gamma) Zn/ insulin unit |
|---|---|---|---|---|---|
| 0.12 | 0.38 | 0.33 | 2 | 0.013 | 0.13 |
| 0.31 | 1 | 0.90 | 5.4 | 0.035 | 0.35 |
| 0.89 | 2.75 | 2.51 | 15.1 | 0.1 | 1 |
| 2.66 | 8 | 7.75 | 46.5 | 0.3 | 3 |
| 4.43 | 12.7 | 12.8 | 77 | 0.5 | 5 |
| 66 | 68.5 | 192.5 | 1155 | 7.5 | 75 |
| 177 | 85.3 | 514.2 | 3086 | 20 | 200 |

TABLE II

Zinc in Solution

| mEq Zn/l | % Zn | mg Zn/ml | mM Zn/l |
|---|---|---|---|
| 0.306 | 0.001 | 0.01 | 0.153 |
| 0.612 | 0.002 | 0.02 | 0.306 |
| 1.53 | 0.005 | 0.05 | 0.765 |
| 3.06 | 0.01 | 0.1 | 1.53 |
| 6.12 | 0.02 | 0.2 | 3.06 |
| 15.3 | 0.05 | 0.5 | 7.65 |
| 30.6 | 0.1 | 1 | 15.3 |
| 61.2 | 0.2 | 2 | 30.6 |
| 153 | 0.5 | 5 | 76.5 |
| 306 | 1 | 10 | 153 |
| 612 | 2 | 20 | 306 |

The following Examples are provided as a means of illustrating the present invention. They are not to be construed as imposing a limitation thereon.

EXAMPLE 1

Preparation of Zinc-modified Human Ultralente Formulations

Humulin Ultralente (Lilly, Indianapolis, Ind.) and Ultralente (Beef) Insulin Extended Insulin Zinc Suspension USP (Novo Nordisk, Bagsvaerd, Denmark), both at a strength of 100 insulin units per ml (U100), were employed. These formulations, containing a total zinc concentration of about 0.15 mg/ml, were either used directly or diluted to an insulin strength of U40 using Sterile Diluent for Ultralente Insulin (Lilly) which contains 0.05 mg/ml zinc. To pre-weighed samples of solid zinc chloride (EM Science, Cherry Hill, N.J.) was added directly the U100 or U40 solutions of Ultralente insulins. Alternatively, to U100 formulations of Humulin Ultralente were added various amounts of concentrated, pH-unadjusted solutions of zinc chloride (100 mg/ml in water) or zinc acetate (J. T. Baker, Phillipsburg, N.J., 200 mg/ml in water). Total zinc levels were either estimated from combination of the calculated zinc levels in the insulin, diluent and reagents or were determined experimentally by atomic absorption spectroscopy.

EXAMPLE 2 pH of Zinc-modified Human Ultralente Formulations

The pHs of current pharmaceutical formulations of Ultralente are all about pH 7.4. Zinc-modified formulations of Ultralente were prepared as described in Example 1 and their pHs were determined. The data is set forth below in Table III.

TABLE III

| Sample | Insulin Strength (U/ml) | Method of Zn Addition | Zn Reagent Used | ªTotal Final mg Zn/ml Formulation | mg Zn/ 100 U Insulin | Final pH |
|---|---|---|---|---|---|---|
| 1 | 40 | None | None | 0.09 | 0.23 | 7.38 |
| 2 | 40 | Solid | Chloride | 0.25 | 0.63 | 7.30 |
| 3 | 40 | Solid | Chloride | 0.59 | 1.48 | 7.03 |
| 4 | 40 | Solid | Chloride | 1.09 | 2.73 | 6.80 |
| 5 | 40 | Solid | Chloride | 2.40 | 6.00 | 6.75 |
| 6 | 40 | Solid | Chloride | 7.31 | 18.28 | 6.34 |
| 7 | 100 | None | None | 0.15 | 0.15 | 7.37 |
| 8 | 100 | Solid | Chloride | 2.60 | 2.60 | 6.84 |
| 9 | 100 | Solid | Chloride | 7.40 | 7.40 | 6.41 |
| 10 | 100 | Solid | Chloride | 12.20 | 12.20 | 6.21 |
| 11 | 97 | Aqueous | Chloride | 1.59 | 1.64 | 6.80 |
| 12 | 94 | Aqueous | Chloride | 2.92 | 3.11 | 6.73 |
| 13 | 93 | Aqueous | Chloride | 3.81 | 4.10 | 6.63 |
| 14 | 91 | Aqueous | Chloride | 4.55 | 5.00 | 6.59 |
| 15 | 83 | Aqueous | Chloride | 8.18 | 9.86 | 6.41 |
| 16 | 91 | Aqueous | Acetate | 5.60 | 6.15 | 6.75 |
| 17 | 83 | Aqueous | Acetate | 10.09 | 12.16 | 6.51 |

ªEstimated

Clearly, the pHs of these formulations drop slightly as the zinc reagent is added. Samples prepared with zinc acetate showed less of a pH drop compared to zinc chloride. In further examples described herein, except for Example 3B, no additional pH adjustments were made to solutions prepared in this manner.

It was found, also, that addition of minute amounts of sodium hydroxide solutions to these zinc-fortified formulations, after addition of the zinc reagents, could be made to raise the pH to a small degree. Adjusting the formulations up toward pH 7.4 by adding larger quantities of sodium hydroxide, however, caused immediate formation of clumpy precipitates, presumably zinc hydroxide-type species, that made the formulations unusable for additional purposes. On the other hand, addition of acidic solutions like hydrochloric acid or acetic acid to lower the pH after preparing the zinc-fortified Ultralentes did not cause any precipitation problems, but HPLC analyses of the supernatants revealed a small, additional percentage of the Ultralente crystals had become solublized during this acidification process. Acidification using dilute acetic acid worked best in minimizing or eliminating the solublization of the insulin, as in Example 3B. Therefore, since minor pH adjustments of these zinc-fortified Ultralente suspensions can be satisfactorily made, this patent should not be limited to only the pH that results when a specific zinc reagent is added.

EXAMPLE 3

Zinc Levels in Zinc-modified Human Ultralente Formulations

A. Three zinc-fortified human Ultralente formulations were prepared like in Sample 8 of Example 2. One ml of each of these three suspensions, with estimated total zinc levels of 0.7 to 2.5 mg per 100 insulin units, and an unaltered Humulin Ultralente insulin formulation were swirled by hand for 30 minutes at 25° C., then stored at 5° C. for 20 hours. Each suspension was then pushed through a 0.2 micron Acrodisc® filter (Gelman Sciences, Ann Arbor, Mich.). The filtrate was diluted with 9 ml of 0.1N HCl. The insoluble crystals remaining on the filter were redissolved by slowly passing 10 ml of 0.1N HCl through each filter. Zinc levels in these solutions were determined by atomic absorption and calculated back to the zinc levels in the original formulation supernatants or insulin crystals. Data from these experiments is set forth in Table IV.

TABLE IV

| Sample | mg/ml Bound Zinc | mg/ml Free Zinc | Percent of Total Zinc in Supernatant |
|---|---|---|---|
| 1 | 0.12 | 0.07 | 36.8% |
| 2 | 0.19 | 0.63 | 76.8% |
| 3 | 0.18 | 1.30 | 87.8% |
| 4 | 0.20 | 2.60 | 92.9% |

This experiment showed that most of the extra added zinc remained in the supernatant and was neither complexed nor covalently bound with the insulin crystals.

B. 20 ml of a formulation containing about 2.5 mg/ml of zinc was prepared like in Sample 8 of Example 2. Half of this suspension (pH 6.81) was left unadjusted while the other half was adjusted to pH 6.15 by adding a small volume of dilute acetic acid. The suspensions were stored at 5° C. At various times, the zinc levels in the supernatants and insoluble crystals were determined as described above. Data from these experiments is set forth in Table V below.

TABLE V

| | Days at 5° C. | mg/ml Bound Zinc | mg/ml Free Zinc | Percent of Total Zn in Supernatant |
|---|---|---|---|---|
| Sample at pH 6.81 | 0 | 0.27 | 2.18 | 89.0% |
| | 2 | 0.26 | 2.75 | 91.4% |
| | 4 | 0.37 | 2.14 | 85.3% |
| | 7 | 0.39 | 2.50 | 86.5% |
| | 10 | 0.35 | 2.50 | 87.7% |
| | 15 | 0.42 | 2.25 | 84.3% |
| | 21 | 0.36 | 2.75 | 88.4% |
| | 28 | 0.35 | 3.25 | 90.3% |
| Sample at pH 6.15 | 0 | 0.29 | 2.14 | 88.1% |
| | 2 | 0.28 | 2.18 | 88.6% |
| | 4 | 0.25 | 2.12 | 89.4% |
| | 7 | 0.40 | 2.50 | 86.2% |
| | 10 | 0.30 | 3.00 | 90.9% |
| | 15 | 0.33 | 2.50 | 88.3% |
| | 21 | 0.35 | 2.50 | 87.7% |
| | 28 | 0.33 | 2.75 | 89.3% |

This experiment showed that pH adjustment with dilute acetic acid did not alter the distribution of zinc between the supernatant and insoluble insulin crystals. It also showed that the zinc distribution did not significantly change during storage. Most of the zinc remained in the supernatant fraction in both of these formulations.

EXAMPLE 4

Stability Of Zinc-modified Human Ultralente Formulations

A. Several zinc-fortified human Ultralente formulations, prepared as described in Example 2, were examined microscopically at 43×magnification. All suspensions showed the typical rhombohedral form of Ultralente crystals found in unaltered formulations. The sizes, shapes and integrity of the crystals in the zinc-modified suspensions were virtually indistinguishable from the unmodified suspension. The presence of significant amounts of extraneous, insoluble non-crystalline particles in these formulations was not detected.

The formulations also showed the same swirling patterns as unaltered Ultralente formulations. After swirling, the crystalline suspensions also showed the same settling characteristics as unaltered Ultralente, both in terms of the time to achieve complete settling of the crystals and the approximate packing volume of the crystals.

B. A zinc-fortified formulation of human Ultralente insulin containing about 7.5 mg/ml of zinc (similar to Sample 9 of Example 2) was prepared. Unmodified Ultralente (Sample 7 of Example 2) was used as a control. Both samples were stored at 5° C. for approximately 1 year. At this time, the insulin crystals were redissolved in dilute hydrochloric acid and evaluated for purity on a reverse-phase high performance liquid chromatography (HPLC) system. A 4.6×250 mm Zorbax C-8 column containing 150-angstrom pore-sized particles was employed at 40° C. The insulin was eluted at a flow rate of 0.7 ml/min in a gradient of acetonitrile containing 0.225M ammonium sulfate at about pH 2.

After 1 year, the purity of the unmodified Ultralente insulin was 96.4%, with several unidentified peaks in the 0.2% range each and the $A^{21}$-desamido insulin peak at about 1%. The Ultralente formulation containing 7.5 mg/ml zinc after 1 year showed an overall insulin purity of 96.8%, with several unidentified peaks in the 0.1–0.2% range and the $A^{21}$-desamido insulin peak at about 1%. A new, unknown peak eluting before insulin but not seen in the unmodified Ultralente sample was present at the 0.3% level.

These experiments demonstrated that zinc-modified formulations retain the stability of the Ultralente crystals in terms of their size and shape. Also, having high levels of zinc in the Ultralente formulation did not significantly alter the chemical purity of the insulin molecule after storage for a year at 5° C.

EXAMPLE 5

Composite Dissolution Assay

This assay is a modification of an earlier published assay found in Graham and Pomeroy, *J. Pharm. Pharmacol.* 36, 427–430 (1983), the teaching of which is hereby incorporated by reference. It uses the rate of insulin crystal dissolution after a significant dilution with a non zinc-binding buffer as a way of predicting the rate at which the crystalline formulation will dissolve after subcutaneous injection into animals. This is because, for insulin suspensions, the rate-limiting step in generating the biological response is predominantly the dissolution rate of the insoluble insulin after injection. Hence, one can predict that an insulin formulation that dissolves more slowly in this assay compared to human Ultralente would likely act more slowly in biological models.

Three zinc-fortified human Ultralente formulations containing 0.35, 0.7 and 2.5 mg/ml zinc were prepared in a manner similar to Sample 8 in Example 2. 0.5 ml portions of these suspensions and 0.5 ml portions of unaltered U100 human and beef Ultralente formulations were each added to 50 ml of a 0.1M tris (tris hydroxymethyl amino methane, Mallinckrodt, Paris, Ky.) pH 7.5 buffer being stirred at 25° C. in an 80-ml glass beaker. At times of 3 and 8 hours, aliquots of the stirred suspensions were removed and passed through a 0.2 micron Acrodisc® filter. The amount of insulin in the filtrate was quantitated by reversed-phase HPLC. Maximal insulin content was determined by HPLC of an unfiltered, acidified aliquot. There was essentially no solubilized insulin at the start of the dissolution assays. The data from these experiments is set forth below in Table VI.

TABLE VI

| Ultralente Species | mg/ml Estimated Zinc Level | Percent of Maximal Insulin Soluble (3 hours) | Percent of Maximal Insulin Soluble (8 hours) |
|---|---|---|---|
| Human | 0.15 | 16.3% | 44.7% |
| Human | 0.35 | 4.5% | 10.7% |
| Human | 0.70 | 2.4% | 6.3% |
| Human | 2.50 | 1.1% | 3.2% |
| Beef | 0.15 | 3.2% | 6.2% |

This experiment demonstrated that unaltered human Ultralente redissolves much faster than unaltered beef Ultralente. It also shows that adding zinc to the human Ultralente to a level of about 0.7 mg per 100 insulin units makes the insulin crystals dissolve at about the same rate as unaltered beef Ultralente. Giving the human Ultralente a zinc level of about 2.5 mg per 100 insulin units endows it with a dissolution rate even slower than unaltered beef Ultralente insulin.

EXAMPLE 6

Continuous-Flow Dissolution Assay

This assay is a modification of flow-through tests reported earlier by Brange, in *Galenics of Insulin*, p. 46, Springer-Verlag, Berlin (1987) and Graham and Pomeroy, *J. Pharm. Pharmacol.* 36, 427–430 (1983), the teachings of which are herein incorporated by reference. 2-ml aliquots of unaltered human and beef Ultralente insulin and a sample of human Ultralente containing about 0.7 mg of zinc per 100 insulin units (as described in Example 5) were each diluted with 48 ml of 0.1M tris buffer at pH 7.5. Each entire 50-ml suspension was immediately passed through a 0.2 micron Acrodisc® filter and washed with 5 ml of water. Each filter was then placed in-line on the eluant tubing of an FPLC system (Pharmacia, Piscataway, N.J.). Fresh 0.1M tris pH 7.5 buffer was pumped through each filter at a flow rate of 2 ml per minute. The absorbance of the eluant beyond the filters was continuously monitored spectroscopically for the elution of insulin for more than two hours at a wavelength of 214 nanometers. Various portions of the eluants were also examined by reversed-phase HPLC to confirm the presence of human or beef insulin.

The insulin in beef Ultralente crystals was only very slowly dissolved in the fresh tris buffer. The elution of beef insulin was confirmed by HPLC analysis of a portion of the eluant. The insulin in unaltered human Ultralente crystals showed a fast rate of dissolution peaking at about 35 minutes and maintained a relatively high dissolution throughout the experiment. The human Ultralente formulation containing 0.7 mg/ml of zinc showed a response very similar to the unaltered human Ultralente sample, not the beef formulation. This suggests the early filtration step in the assay removed all the unbound zinc from this formulation and the remaining crystals behaved just like the unaltered human Ultralente crystals. This data also dramatically demonstrates the inherent difference in the dissolution rates of human and beef insulin crystals. Data from these experiments are set forth below in Table VII.

TABLE VII

RELATIVE ABSORBANCE

| TIME (minutes) | BEEF Ultralente | HUMAN Ultralente | HUMAN Ultralente, 0.7 mg/ml Zn |
|---|---|---|---|
| 0 | 0 | 0 | 0 |
| 2.5 | 12.5 | 3.5 | 12.5 |
| 5 | 9.0 | 8.0 | 11.5 |
| 10 | 8.0 | 23.0 | 19.0 |
| 15 | 7.8 | 38.0 | 31.7 |
| 20 | 7.9 | 52.0 | 45.0 |
| 25 | 8.0 | 59.0 | 60.0 |
| 30 | 7.4 | 63.0 | 72.0 |
| 35 | 8.1 | 64.0 | 79.5 |
| 40 | 8.0 | 61.0 | 79.0 |
| 45 | 8.3 | 57.5 | 73.0 |
| 50 | 7.8 | 52.0 | 68.0 |
| 55 | 8.2 | 45.5 | 60.0 |
| 60 | 8.5 | 40.0 | 52.2 |
| 65 | 8.5 | 36.0 | 45.5 |
| 70 | 8.8 | 31.5 | 39.5 |
| 75 | 9.0 | 29.5 | 36.3 |
| 80 | 9.7 | 26.0 | 25.0 |
| 90 | 9.6 | 23.0 | 22.1 |
| 100 | 10.4 | 20.2 | 22.1 |
| 110 | 11.0 | 18.5 | 24.3 |
| 120 | 11.2 | 16.6 | 24.0 |
| 130 | 12.0 | 15.1 | 21.6 |

EXAMPLE 7

Rabbit Assays of Ultralente Formulations

Beef Ultralente (U40) and human Ultralente formulations of U40 strength prepared as shown in Samples 1–6 of Example 2 were tested in a normal rabbit model. The rabbits used in this example were New Zealand Whites, mostly female, all weighing 2.7–4 kg, 0.5–4 years of age and fasted 16 hours prior to administration of sample. The insulin suspensions were each injected into 10 rabbits subcutaneously at the back of the neck at a dose of 0.2 units per kilogram. At various times, 100 ul volumes of blood were obtained from the marginal ear veins, mixed with 900 ul volumes of anticoagulant (EDTA-sodium fluoride) and analyzed for glucose content. The glucose values were standardized to reflect percent of original blood glucose measured prior to sample injection. The data from these experiments is set forth in Table VIII.

TABLE VIII

| Sample | Ultralente Species | mg/ml Estimated Zinc Level | % Original Blood Glucose Hours after Injection | | | |
|---|---|---|---|---|---|---|
| | | | 1 | 2 | 4 | 6 |
| 1 | Human | 0.09 | 60.6 | 65.2 | 89.0 | 90.4 |
| 2 | Human | 0.25 | 56.7 | 67.8 | 91.4 | 91.4 |
| 3 | Human | 0.59 | 60.4 | 58.9 | 78.1 | 85.5 |
| 4 | Human | 1.07 | 81.8 | 78.6 | 95.6 | 95.2 |
| 5 | Human | 2.40 | 92.8 | 80.9 | 80.3 | 88.6 |
| 6 | Human | 7.31 | 96.0 | 84.1 | 80.9 | 85.9 |
| 7 | Beef | 0.15 | 60.1 | 68.7 | 96.7 | 95.7 |

The time action profile in the rabbit model is much shorter than in humans. This time-action compression led to the inability of this model to show a significant difference between the unaltered human and beef Ultralente formulations (Sample 1 vs. 7). Despite this limitation, this experiment shows that the biological action of human Ultralente insulin is dramatically altered when sufficient zinc is added to the formulation. As shown in Samples 4–6, the onset of a strong biological response is delayed beyond 1 hour, giving a nadir of between 2 and 4 hours. The maximal drop in blood glucose is also diminished, from about 40% in Samples 1–3 (1 hour nadir) to only about a 20 % drop in Samples 4–6 (2–4 hour nadir). Hence, the formulations with sufficient zinc content clearly showed a prolonged time action much slower than either the unaltered human or beef Ultralente formulations.

I claim:

1. A formulation of human insulin comprising a suspension of human Ultralente insulin crystals in a total formulation zinc concentration of between about 0.5 milligrams to about 20 milligrams per 100 units of insulin wherein the formulation does not contain proteins other than insulin.

2. The insulin formulation of claim 1 wherein the pH is between about 6.0 and 7.4.

3. The insulin formulation of claim 2 wherein the formulation further comprises preservatives.

4. The insulin formulation of claim 3 wherein the formulation further comprises isotonicity agents.

5. The insulin formulation of claim 4 wherein the formulation further comprises a buffer.

6. The insulin formulation of claim 5 wherein the formulation comprises a total formulation zinc concentration of between about 0.5 milligrams to about 7 milligrams per 100 units of insulin.

7. The insulin formulation of claim 6 wherein the formulation pH is between about 6.2 to about 7.2.

8. The insulin formulation of claim 7 wherein the preservative is methyl paraben.

9. The insulin formulation of claim 8 wherein the isotonicity agent is sodium chloride.

10. The insulin formulation of claim 5 wherein the buffer is acetate.

11. A method for making the insulin formulation of claim 1, said method comprising combining zinc with Ultralente insulin crystals.

12. The method of claim 11 wherein the Ultralente insulin is in the form of an aqueous suspension.

13. The method of claim 11 wherein the zinc used is a zinc salt selected form the group consisting of zinc acetate, zinc bromide, zinc chloride, zinc iodide, zinc fluoride and zinc sulfate.

14. The method of claim 11 wherein the zinc used is a solid form selected from the group consisting of zinc chloride and zinc acetate.

15. The method of claim 11 wherein the zinc used is a solution selected from the group consisting of zinc chloride and zinc acetate.

16. The method of claim 11 wherein pH adjustments are made to the formulation after the zinc and Ultralente insulin are combined.

17. The insulin formulation produced by the method of claim 11.

18. A method of treating diabetes mellitus in human patients, said method comprising administering to said human patient a therapeutically acceptable amount of the insulin formulation of claim 1 via subcutaneous injection.

19. The method of claim 18 wherein said subcutaneous injection is administered one time per day.

* * * * *

UNITED STATES PATENT AND TRADEMARK OFFICE
CERTIFICATE OF CORRECTION

PATENT NO. : 5,534,488

DATED : July 9, 1996

INVENTOR(S) : James A. Hoffmann

It is certified that error appears in the above-indentified patent and that said Letters Patent is hereby corrected as shown below:

Claim 14, line 2 (Column 12, line 48), following "solid" delete "form".

Signed and Sealed this

Twenty-ninth Day of October 1996

Attest:

BRUCE LEHMAN

Attesting Officer     Commissioner of Patents and Trademarks